United States Patent [19]
Dong et al.

[11] Patent Number: 5,773,455
[45] Date of Patent: Jun. 30, 1998

[54] INHIBITORS OF PRENYL TRANSFERASES

[75] Inventors: Zheng Xin Dong, Framingham; Sun H. Kim, Needham, both of Mass.

[73] Assignee: Biomeasure, Incorporated, Milford, Mass.

[21] Appl. No.: 672,474

[22] Filed: Jun. 28, 1996

[51] Int. Cl.$^6$ .......................... A01N 43/78; C07D 277/04
[52] U.S. Cl. ............................................. 514/365; 548/200
[58] Field of Search .............................. 548/200; 514/365

[56] References Cited

U.S. PATENT DOCUMENTS 5,439,918  8/1995  deSolms et al. .
5,491,614  2/1996  deSolms et al. .

FOREIGN PATENT DOCUMENTS 0 618 221 A2  10/1994  European Pat. Off. .
0 696 593 A2  2/1996   European Pat. Off. .

OTHER PUBLICATIONS

Nagano et al, Chemical Abstract, vol. 107, p. 236699 (1987) "Preparation of Benzoyltihazolidinecarboxamides . . .".

Kimura et al, Chemical Abstract, vol. 125, p. 115155 (1996) "Preparation of Tripeptides . . . HIV Protease Inhibitor".

Bishop et al., "Novel Tricyclic Inhibitors of Farnesyl Protein Transferase", The Journal of Biological Chemistry 270:30611–30618, 1995.

Bhide et al., "Rational Design of Potent Carboxylic Acid Based Bisubtrate Inhibitors of Ras Farnesyl Protein Transferase" Bioorganic & Medicinal Chemistry Letters 4:2107–2112, 1994.

Buss et al., "Farnesyl Transferase Inhibitors: The Successes and Surprises of a New Class of Potential Cancer Chemotherapeutics", Chemistry & Biology 2:787–791, Dec. 1995.

Clerc et al., "Constrained Analogs of KCVFM With Improved Inhibitory Properties Against Farnesyl Transferase" Bioorganic & Medicinal Chemistry Letters 16:1779–1784, 1995.

deSolms et al., "Pseudodipeptide Inhibitors of Protein Farnesyltransferase", J. Med. Chem. 38:3967–3971, 1995.

Garcia et al., "Peptidomimetic Inhibitors of Ras Farnesylation and Function in Whole Cells", The Journal of Biological Chemistry 268:18415–18418, 1993.

Graham et al., "Pseudopeptide Inhibitors of Ras Farnesyl–Protein Transferase", J. Med. Chem. 37:725–732, 1994.

Gibbs et al., "Farnesyltransferase Inhibitors: Ras Research Yields a Potential Cancer Therapeutic", Cell 77:175–178, Apr. 22, 1994.

Harrington et al., "Cysteine and Methionine Linked by Carbon Pseudopeptides Inhibit Farnesyl Transferase", Bioorganic & Medicinal Chemistry Letters 4:2775–2780, 1994.

Hunt et al., "Potent, Cell Active, Non–Thiol Tetrapeptide Inhibitors of Farnesyltransferase", J. Med. Chem. 39:353–358, 1996.

James et al., "Polylysine and CVIM Sequences of k–RasB Dictate Specificity of Prenylation and Confer Resistance to Benzodiazepine Peptidomimetic in Vitro", The Journal of Biological Chem. 270:6221–6226, 1995.

Koblan et al., "NMR Studies of Novel Inhibitors Bound to Farnesyl–Protein Transferase", Protein Science 4:681–488, 1995.

Kohl et al., "Development of Inhibitors of Protein Farnesylation as Potential Chemotherapeutic Agents", Journal of Cellular Biochemistry 22:145–150, 1995.

Kohl et al., "Inhibition of Farnesyltransferase Induces Regression of Mammary and Salivary Carcinomas in Ras Transgenic Mice", Nature Medicine 1:792–797, 1995.

Kohl et al., "Inhibition of Ras Function in Vitro and in Vivo Using Inhibitors of Farnesyl–Protein Transferase", Methods in Enzymology 255:378–386, 1989.

Kohl et al., "Selective Inhibition of ras–Dependent Transformation by a Farnesyltransferase Inhibitor", Science 260:1934–1937, Jun. 25, 1993.

Leftheris et al., "Development of Highly Potent Inhibitors of Ras Faranesyltransferase Possessing Cellular and in Vivo Activity", J. Med. Chem. 39:224–236, 1996.

Lerner et al., "Ras CAAX Peptidomimetic FTI–277 Selectively Blocks Oncogenic Ras Signaling by Inducing Cytoplasmic Accumulation of Inactive Ras–Raf Complexes", The J. of Biological Chem. 270:26802–26806, 1996.

(List continued on next page.)

*Primary Examiner*—Mukund J. Shah
*Assistant Examiner*—Tamthom T. Ngo
*Attorney, Agent, or Firm*—Fish & Richardson; William McGowan; John D. Conway

[57] ABSTRACT

A family of compounds capable of inhibiting the activity of prenyl transferases. The compounds are covered by one of the two following formulas:

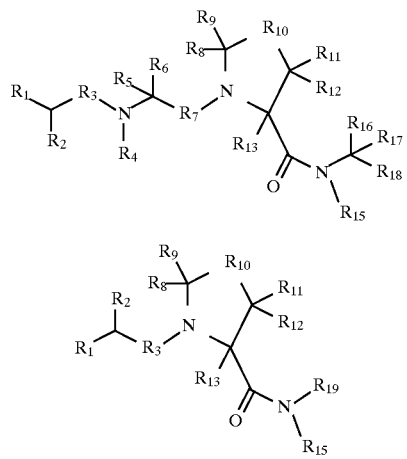

Each of the R groups is defined in the disclosure.

23 Claims, No Drawings

OTHER PUBLICATIONS

Li et al., "Total Synthesis of the Antitumor Depsipeptide FR–901, 228", J. Am. Chem. Soc. 118:7237–7238, 1996.

Nagasu et al., "Inhibition of Human Tumor Xenograft Growth by Treatment with the Farnesyl Transferase Inhibitor B956", Cancer Research 55:5310–5314, Nov. 15, 1995.

Nigam et al., "Potent Inhibition of Human Tumor $p21^{ras}$ Farnesyltransferase by $A_1A_2$–lacking $p21^{ras}$... ", The Journal of Biological Chemistry 268:20695–20698, 1993.

Patel et al., "Phenol Based Tripeptide Inhibitors of Ras Farnesyl Protein Transferase", Bioorganic & Medicinal Chemistry Letters 4:1883–1888, 1994.

Qian et al., "Design and Structural Requirements of Potent Peptidomimetic Inhibitors of $p21^{ras}$ Farnesyltransferase", The Journal of Biological Chemistry 269:12410–12413, 1994.

Qian et al., "Design and Synthesis of Non–Peptide Ras CAAX Mimetics as Potent Farnesyltransferase Inhibitors" J. Med. Chem. 39:217–223, 1996.

Reiss et al., "Sequence Requirement for Peptide Recognition by Rat Brain $p21^{ras}$ Protein Farnesyltransferase", Proc. Natl. Acad. Sci. USA 88:732–736, 1991.

Sepp–Lorenzino et al., "A Peptidomimetic Inhibitor of Farnesyl:Protein Transferase Blocks the Anchorage–Dependent and –Independent Growth of Human Tumor Cell Lines", Cancer Research 55:5302–5309, 1995.

Singh et al., "Fusidienol: A Novel Inhibitor of Ras Farnesyl–Protein Transferase from Fusidium Griseum", Tetrahedron Letters 35:4693–4696, 1994.

Williams et al., "2–Substituted Piperazines as Constrained Amino Acids. Application to the Synthesis of Potent, Non Carboxylic Acid Inhibitors of Farnesyltransferase", J. of Medicinal Chemistry 39:1345–1348, 1996.

James et al., "Benzodiazepine Peptidomimetics: Potent Inhibitors of Ras Farnesylation in Animal Cells", Science 260:1937–1942, Jun. 25, 1993.

Byk et al., "Local Constrained Shifty Pseudopeptides inhibitgors of Ras–Farnesyl Transferase", Bioorganic & Medicinal Chemistry Letters 5:2677–2682, 1995.

INHIBITORS OF PRENYL TRANSFERASES

BACKGROUND OF THE INVENTION

The Ras family of proteins are important in the signal transduction pathway modulating cell growth. The protein is produced in the ribosome, released into the cytosol, and post-translationally modified. The first step in the series of post-translational modifications is the alkylation of $Cys^{168}$ with farnesyl or geranylgeranyl pyrophosphate in a reaction catalyzed by prenyl transferase enzymes such as farnesyl transferase and geranylgeranyl transferase (Hancock, J. F., et al., Cell 57:1167–1177 (1989)). Subsequently, the three C-terminal amino acids are cleaved (Gutierrez, L., et al., EMBO J. 8:1093–1098 (1989)), and the terminal Cys is converted to a methyl ester (Clark, S., et al., Proc. Nat'l Acad. Sci. (USA) 85:4643–4647 (1988)). Some forms of Ras are also reversibly palmitoylated on cysteine residues immediately N-terminal to $Cys^{168}$ (Buss, J. E., et al., Mol. Cell. Biol. 6:116–122 (1986)). It is believed that these modifications increase the hydrophobicity of the C-terminal region of Ras, causing it to localize at the surface of the cell membrane. Localization of Ras to the cell membrane is necessary for signal transduction (Willumsen, B. M., et al., Science 310:583–586 (1984)).

Oncogenic forms of Ras are observed in a relatively large number of cancers including over 50 percent of colon cancers and over 90 percent of pancreatic cancers (Bos, J. L., Cancer Research 49:4682–4689 (1989)). These observations suggest that intervention in the function of Ras mediated signal transduction may be useful in the treatment of cancer.

Previously, it has been shown that the C-terminal tetrapeptide of Ras is a "CAAX" motif (wherein C is cysteine, A is an aliphatic amino acid, and X is any amino acid). Tetrapeptides having this structure have been shown to be inhibitors of prenyl transferases (Reiss, et al., Cell 62:81–88 (1990)). Poor potency of these early farnesyl transferase inhibitors has prompted the search for new inhibitors with more favorable pharmacokinetic behavior (James, G. L., et al., Science 260:1937–1942 (1993); Kohl, N. E., et al., Proc. Nat'l Acad. Sci. USA 91:9141–9145 (1994); deSolms, S. J., et al., J. Med. Chem. 38:3967–3971 (1995); Nagasu, T., et al., Cancer Research 55:5310–5314 (1995); Lerner, E. C., et al., J. Biol. Chem. 270:26802–26806 (1995); Lerner, E. C., et al., J. Biol. Chem. 270:26770 (1995); and James, et al., Proc. Natl. Acad. Sci. USA 93:4454 (1996)).

Recently, it has been shown that a prenyl transferase inhibitor can block growth of Ras-dependent tumors in nude mice (Kohl, N. E., et al., Proc. Nat'l Acad. Sci. USA 91:9141–9145 (1994)). In addition, it has been shown that over 70 percent of a large sampling of tumor cell lines are inhibited by prenyl transferase inhibitors with selectivity over non-transformed epithelial cells (Sepp-Lorenzino, I., et al., Cancer Research, 55:5302–5309 (1995)).

SUMMARY OF THE INVENTION

In one aspect, the invention features a compound of formula I or formula II

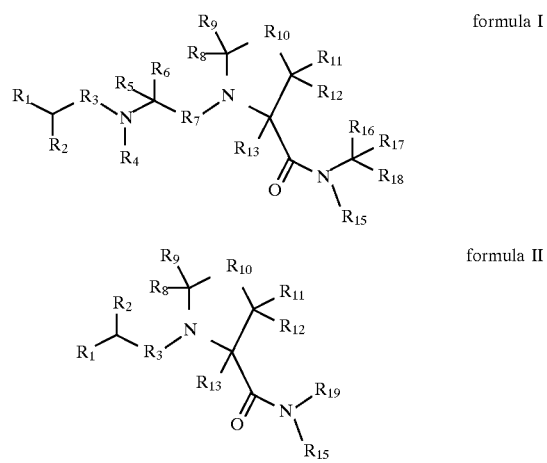

wherein
$R_1$ is H or $NR_{20}R_{21}$;
$R_2$ is $(CH_2)_mSR_{22}$, $(CH_2)_mSSR_{22}$, substituted or unsubstituted heterocycle, or substituted or unsubstituted heterocycle lower alkyl, where m is 1–6 and the substituent is lower alkyl, lower alkenyl, aryl, or aryl lower alkyl;
each of $R_3$ and $R_7$, independently, is $CH_2$ or $C(O)$;
each of $R_4$ and $R_{15}$, independently, is H or lower alkyl;
each of $R_5$ and $R_{16}$, independently, is H or a substituted or unsubstituted moiety selected from lower alkyl, thio lower alkyl, lower alkenyl, thio lower alkenyl, cycloalkyl, cycloalkyl lower alkyl, aryl, and aryl lower alkyl, where the substituent is lower alkyl, hydroxy, halo, $C(O)NR_{23}R_{24}$, or COOH;
each of $R_6$, $R_8$, $R_9$, $R_{11}$, $R_{12}$, $R_{13}$, and $R_{17}$, independently, is H or a substituted or unsubstituted moiety selected from lower alkyl, lower alkenyl, thio lower alkyl, cycloalkyl, aryl, and aryl lower alkyl, where the substituent is lower alkyl, halo, hydroxy, $C(O)NR_{25}R_{26}$, or COOH;
$R_{10}$ is S, SO, or $SO_2$;
$R_{18}$ is $COOR_{27}$ or $C(O)NR_{28}R_{29}$, or, together with $R_{16}$, forms $—COOCH_2CH_2—$.
$R_{19}$ is a substituted (with one or more substituents; same below) or unsubstituted moiety selected from lower alkyl, lower alkenyl, aryl, and aryl lower alkyl, where the substituent is lower alkyl (e.g., an alkyl group can also be deemed as a substituent too), halo, or alkoxy; and
each of $R_{20}$, $R_{21}$, $R_{22}$, $R_{23}$, $R_{24}$, $R_{25}$, $R_{26}$, $R_{27}$, $R_{28}$, and $R_{29}$, independently, is H or lower alkyl; provided that if $R_2$ is $(CH_2)_mSH$ and $R_5$ is thio lower alkyl, the free thio groups of $R_2$ and $R_5$ can form a disulfide bond; or a pharmaceutically acceptable salt thereof.

In one embodiment, the compound is of formula I where $R_2$ is $(CH_2)_mSR_{22}$, heterocycle, or heterocycle lower alkyl; each of $R_4$ and $R_{15}$, independently, is H; $R_5$ is lower alkyl; $R_6$ is H; each of $R_8$, $R_9$, $R_{11}$, and $R_{12}$, independently, is H or lower alkyl; $R_{10}$ is S; $R_{13}$ is H; $R_{16}$ is lower alkyl or substituted thio lower alkyl wherein the substituent is lower alkyl; and $R_{17}$ is H. In this embodiment, $R_1$ can be $NR_{20}R_{21}$ (e.g., $NH_2$); $R_2$ can be $(CH_2)_mSR_{22}$ (e.g., $CH_2SH$); $R_3$ can be $CH_2$; each of $R_8$ and $R_9$, independently, can be H; and $R_{18}$ can be $COOR_{27}$; furthermore, $R_5$ can be $CH(CH_3)(CH_2CH_3)$, $(CH_2)_3CH_3$, $CH(CH_3)_2$, or $C(CH_3)_3$; each of $R_{11}$ and $R_{12}$, independently, can be $CH_3$; $R_{16}$ can be $(CH_2)$ $_2SCH_3$ or $CH_2CH(CH_3)_2$; and $R_{18}$ can be COOH or COOCH$_3$. In the same embodiment, $R_1$ can be H; $R_2$ can be heterocycle or heterocycle lower alkyl; $R_3$ can be CH$_2$; each of $R_8$ and $R_9$, independently, can be H; and $R_{18}$ can be COOR$_{27}$ where $R_{27}$ is H or lower alkyl; furthermore, $R_2$ can be imidazolyl or imidazolyl lower alkyl; $R_5$ can be CH(CH$_3$)(CH$_2$CH$_3$), CH(CH$_3$)$_2$, or C(CH$_3$)$_3$; each of $R_{11}$ and $R_{12}$, independently, can be CH$_3$; $R_{16}$ can be (CH$_2$)$_2$SCH$_3$, (CH$_2$)$_3$CH$_3$, or CH$_2$CH(CH$_3$)$_2$; and $R_{18}$ can be COOH or COOCH$_3$.

In another embodiment, the compound is of formula II where $R_2$ is (CH$_2$)$_m$SR$_{20}$, heterocycle, or heterocycle lower alkyl; each of $R_8$, $R_9$, $R_{11}$, and $R_{12}$, independently, is H or lower alkyl; $R_{10}$ is S; $R_{13}$ is H; and $R_{15}$ is H. In this embodiment, $R_1$ can be NR$_{20}$R$_{21}$; $R_2$ can be (CH$_2$)$_m$SR$_{22}$; $R_3$ can be CH$_2$; each of $R_8$ and $R_9$, independently, can be H; and $R_{19}$ can be substituted or unsubstituted aryl lower alkyl wherein the substituent is halo or lower alkyl; furthermore, $R_1$ can be NH$_2$; $R_2$ can be CH$_2$SH; each of $R_{11}$ and $R_{12}$, independently, can be CH$_3$; and $R_{19}$ is 2,3-dichlorobenzyl or 1-naphthylmethyl. In the same embodiment, $R_1$ can be H; $R_2$ can be heterocycle, or heterocycle lower alkyl; $R_3$ can be CH$_2$; each of $R_8$ and $R_9$, independently, can be H; and $R_{19}$ can be substituted or unsubstituted aryl lower alkyl wherein the substituent is halo or lower alkyl; furhtermoe, $R_2$ can be imidazolyl or imidazolyl lower alkyl; each of $R_{11}$ and $R_{12}$, independently, can be CH$_3$; and $R_{19}$ can be 2,3-dichlorobenzyl or 1-napthylmethyl.

Examples of the present invention include the following:

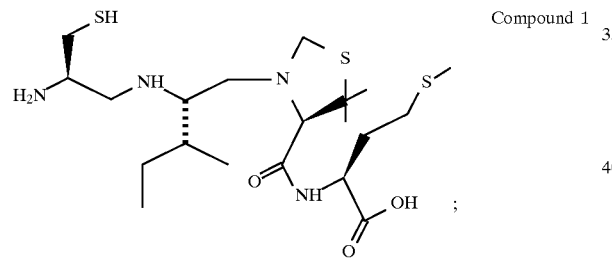

Compound 1

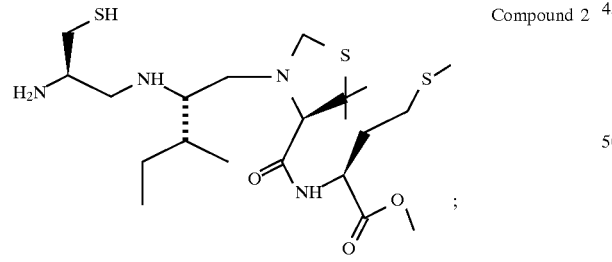

Compound 2

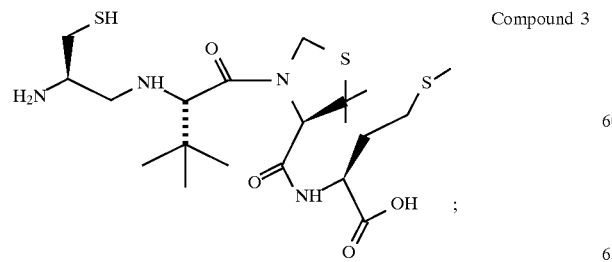

Compound 3

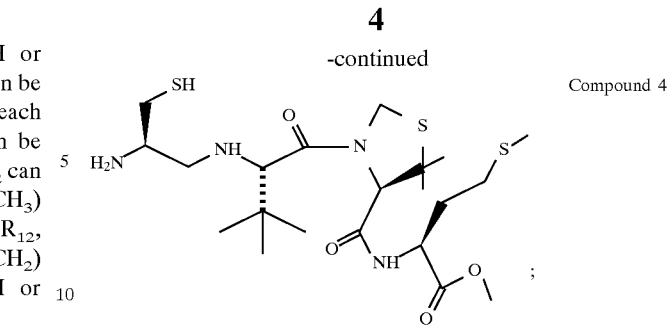

Compound 4

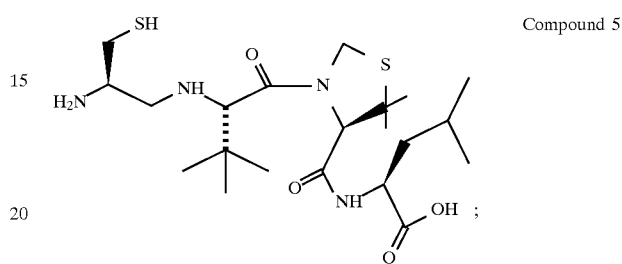

Compound 5

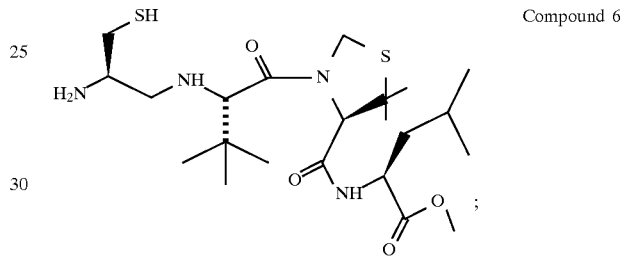

Compound 6

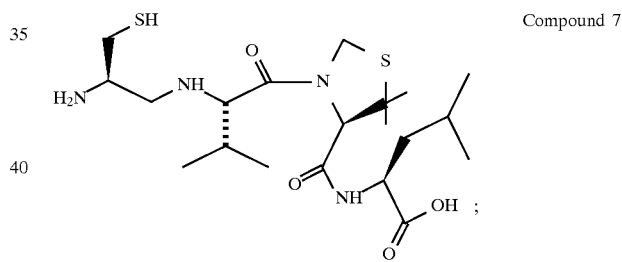

Compound 7

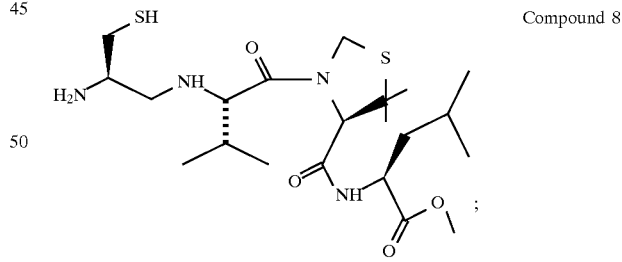

Compound 8

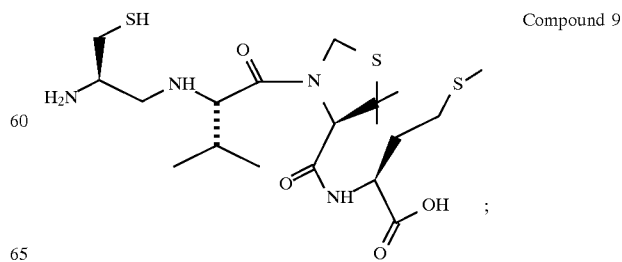

Compound 9

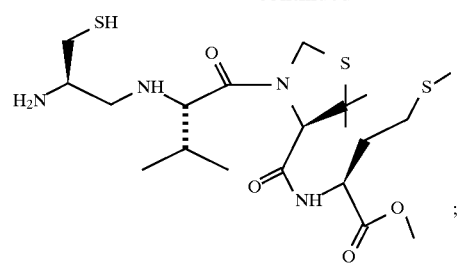
Compound 10
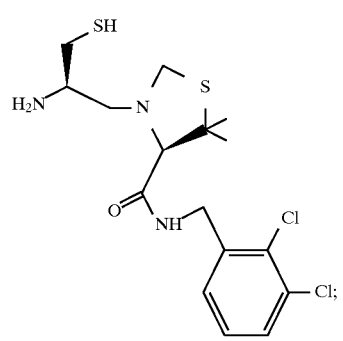
Compound 11
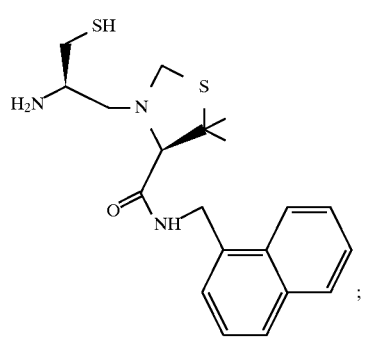
Compound 12
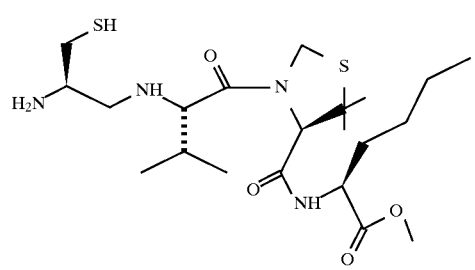
Compound 13
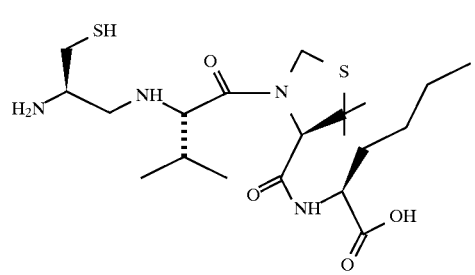
Compound 14
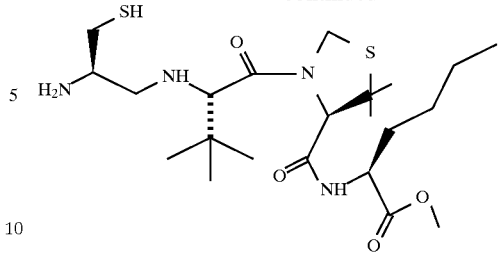
Compound 15
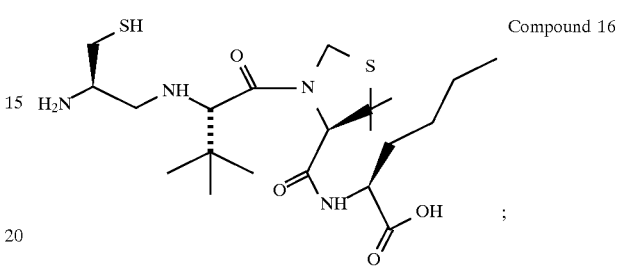
Compound 16
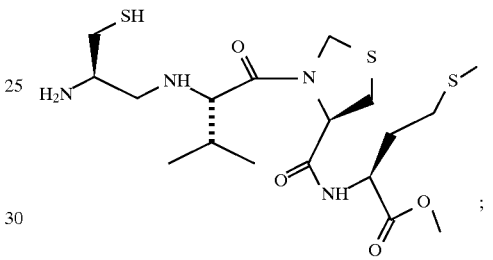
Compound 17
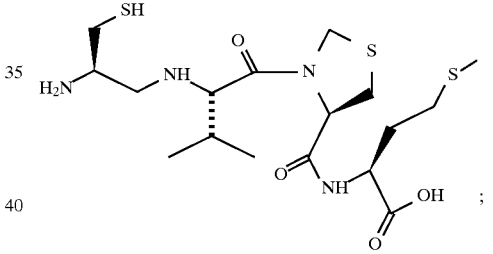
Compound 18
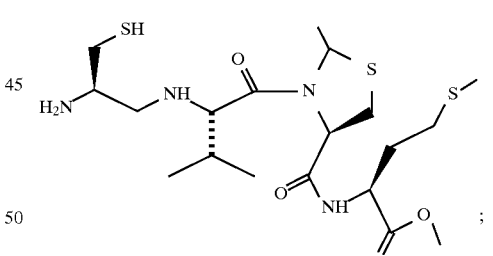
Compound 19
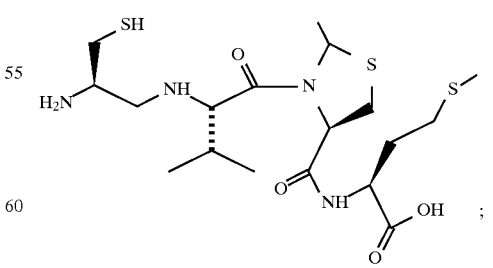
Compound 20
and

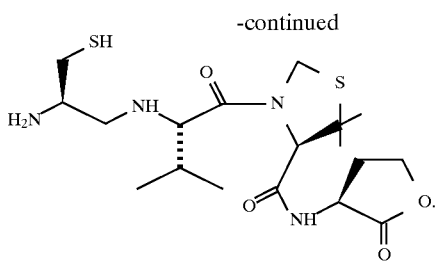

Compound 21

In another aspect, the invention features a dimeric compound consisting of a first moiety and a second moiety, wherein each of the first and second moieties, independently, is of formula I or formula II shown above except that each $R_2$ of the first moiety and $R_2$ of the second moiety, independently, are —$(CH_2)_mS$— and form a disulfide bond; or a pharmaceutically acceptable salt thereof. The first and second moieties can be identical or different. Indeed, $R_2$ of the first moiety and $R_2$ of the second moiety can also be identical or different. An example of such a dimeric compound is shown below:

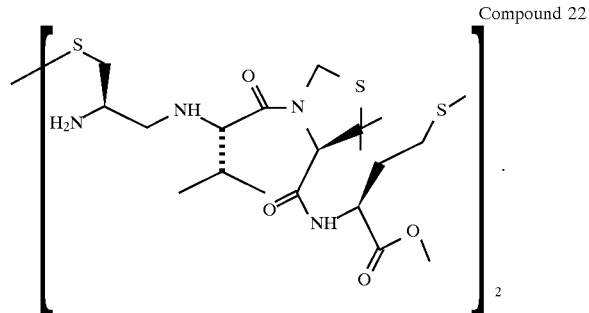

Compound 22

The compounds of the present invention may have asymmetric centers and occur as racemates, racemic mixtures, and as individual diastereomers, with all possible isomers, including optical isomers, being included in the present invention. For simplicity, where no specific configuration is depicted in the structural formulae, it is understood that all enantiometric forms and mixtures thereof are represented.

As used herein, "lower alkyl" is intended to include saturated aliphatic hydrocarbon groups having 1–6 carbon atoms. Examples of lower alkyl groups include methyl, ethyl, propyl, isopropyl, butyl, isobutyl, t-butyl, and the like. "Lower alkenyl" groups include those groups having 2–6 carbon atoms and having one or several double bonds. Examples of alkenyl groups include vinyl, allyl, isopropenyl, butenyl, pentenyl, hexenyl, 1-propenyl, 2-butenyl, 2-methyl-2-butenyl, isoprenyl, and the like. "Lower alkoxy" groups include those groups having 1–6 carbons. Examples of lower alkoxy groups include methoxy, ethoxy, propoxy, isopropoxy, and the like. All alkyl, alkenyl, and alkoxy groups may be branched or straight chained, but are noncyclic. The term "cycloalkyl" means a 3–7 carbon ring. Examples of cycloalkyl groups include cyclopropyl, cyclobutyl, cyclopentyl, cyclohexyl, and cycloheptyl. The term "halo" means chloro, bromo, iodo, or fluoro. The terms "heterocycle lower alkyl," "thio lower alkyl," "thio lower alkenyl," "aryl lower alkyl," and "hydroxy lower alkyl," are substituted, respectively, with one to three heterocycle, thio, thio, aryl, and hydroxy groups.

As used herein, "aryl" is intended to include any stable monocyclic, bicyclic, or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl, and the like.

The term heterocycle, as used herein, represents a stable 5- to 7-membered monocyclic or stable 8- to 11-membered bicyclic or stable 11 to 15-membered tricyclic heterocyclic ring which is either saturated or unsaturated, and which consists of carbon atoms and from one to four heteroatoms selected from the group consisting of N, O and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thiazolidinyl, thienofuryl, thienothienyl, thienyl, and the like.

When a group is substituted, it may be substituted one to four times. The various substituents may be attached to carbon atoms or to heteroatoms (e.g., S, N, or O).

The compounds of this invention can be provided in the form of pharmaceutically acceptable salts. Acceptable salts include, but are not limited to acid addition salts of inorganic acids such as acetate, maleate, fumarate, tartrate, succinate, citrate, lactate, methanesulfonate, p-toluenesulfonate, pamoate, salicylate, oxalate, and stearate. Also within the scope of the present invention, where applicable, are salts formed from bases such as sodium or potassium hydroxide. For further examples of pharmaceutically acceptable salts see, "Pharmaceutical Salts," J. Pharm. Sci. 66:1 (1977).

In a still further aspect, the invention features a method of inhibiting prenyl transferases (e.g., farnesyl transferase or geranylgeranyl transferase) in a subject, e.g., a mammal such as a human, by administering to the subject a therapeutically effective amount of a compound of formula I or formula II. In particular, the present invention also covers a method of treating restenosis or tissue proliferative diseases (i.e., tumor) in a subject by administering to the subject a therapeutically effective amount of a compound or its salt. Examples of tissue proliferative disease include both those associated with benign (e.g., non-malignant) cell proliferation such as fibrosis, benign prostatic hyperplasia, atherosclerosis, and restenosis, and those associated with malignant cell proliferation, such as cancer (e.g., ras mutant tumors). Examples of treatable tumors include breast, colon, pancreas, prostate, lung, ovarian, epidermal, and hematopoietic cancers (Sepp-Lorenzino, I., et al., Cancer Research 55:5302 (1995)).

A therapeutically effective amount of a compound of this invention and a pharmaceutically acceptable carrier substance (e.g., magnesium carbonate, lactose, or a phospholipid with which the therapeutic compound can form a micelle) together form a pharmaceutical composition (e.g., a pill, tablet, capsule, or liquid) for administration (e.g., orally, intravenously, transdermally, or subcutaneously) to a subject in need of the compound. The pill, tablet, or capsule can be coated with a substance capable of protecting the composition from the gastric acid or intestinal enzymes in the subject's stomach for a period of time sufficient to allow the composition to pass undigested into the subject's small intestine.

The dose of a compound of the present invention for treating the above-mentioned diseases or disorders varies depending upon the manner of administration, the age and the body weight of the subject, and the condition of the subject to be treated, and ultimately will be decided by the attending physician or veterinarian. Such an amount of the compound as determined by the attending physician or veterinarian is referred to herein as a "therapeutically effective amount."

Also contemplated within the scope of the invention are pharmaceutical preparations of compounds of formula I and formula II, methods of preparing the compounds of formula I or formula II, and the novel chemical intermediates used in these syntheses as described herein.

Other features and advantages of the present invention will be apparent from the detailed description of the invention and from the claims.

DETAILED DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

The following is a description of the synthesis of Compounds 1 to 12. Other compounds of the invention can be prepared in an analogous manner by a person of ordinary skill in the art.

The compounds of this invention were prepared by using standard solution phase peptide synthesis methodologies as well as other standard manipulations such as ester hydrolysis and reductive akylation of an amine by an aldehyde, e.g., as described in Greenstein, et al., Chemistry of the Amino Acids, Vols. 1–3 (J. Wiley, New York (1961)); and M. Bodanszky, et al.., The Practice of Peptide Synthesis (Springer-Verlag, 1984)). For amide formation reactions, EDC/HOBt or HBTU/DIEA/DMF was used as the coupling agent. Deprotection of the protecting groups was done by using TFA/DCM. The reducing agent used in the reductive alkylation of an amine was sodium cyanoborohydride. The final products were purified by using preparative HPLC and analyzed by $^1$H NMR or mass spectroscopy.

EXAMPLE 1

N-[N'-[2(S)-(2(R)-Amino-3-mercaptopropylamine)-3(S)-methylpentyl]-L-5,5-dimethylthiazolidine-4-carboxyl]-methionine (Compound 1)

(a) N-α-(tert-Butoxycarbonyl)-L-5,5-dimethylthiazolidine-4-carboxylic acid

A solution of L-5,5-dimethylthiazolidine-4-carboxylic acid (2.5 g, 15.5 mmol) in water (10 mL), dioxane (20 mL), and 2N NaOH (7.8 mL) was stirred and cooled in an ice-water bath. Di-tert-butyl dicarbonate (3.72 g, 17.1 mmol) was added and stirring was continued at room temperature overnight. The solution was concentrated in vacuo to about 25 mL and ethyl acetate (EtOAc; 30 mL) was added. The pH of the solution was adjusted to 2 at 0° C. by addition of 2N HCl. The organic layer was separated, and the aqueous layer was extracted with EtOAc (20 mL). The two organic layers were combined, washed with water (2 times), dried over anhydrous MgSO$_4$, filtered, and evaporated in vacuo. The title compound, as a white solid (3.60 g; Yield: 89%), was obtained, and it was used in the next reaction without further purification. $^1$H NMR (300 MHz, CDCl$_3$) δ 4.68 (m, 2H), 4.39 (s, 1H) 4.23 (s, 1H), 1.60-1.40 (m, 15H).

(b) N-[(tert -Butoxycarbonyl)-L-5,5-dimethylthiazolidine-4-carboxylic]-L-methionine methyl ester A solution of N-(tert-butoxycarbonyl)-L-5,5-dimethylthiazolidine-4-carboxylic acid (1.00 g, 3.83 mmol), 1-(3-dimethylaminopropyl)-3-ethylcarbodiimide hydrochloride (EDC; 0.734 g; 3.83 mmol), 1-hydroxybenzotriazole (HOBt; 0.517 g; 3.83 mmol), and diisopropylethylamine (DIEA; 0.495 g; 3.83 mmol) in dichloromethane (DCM; 20 mL) was stirred at 0° C. for 10 minutes. To this solution was added methionine methyl ester hydrochloride (0.765 g, 3.83 mmol). The mixture was warmed to room temperature and stirred overnight. The solvent was removed in vacuo. The residue was dissolved in EtOAc, washed with 5% citric acid (2 times), 5% Na$_2$CO$_3$ (2 times), and brine (2 times), dried over anhydrous MgSo$_4$, and filtered. The residue obtained after concentration was further purified by column chromatography on silica, eluting with hexanes/EtOAc (2:1). The title compound, as a white solid (1.09 g; Yield: 70%), was obtained. $^1$H NMR (300 MHz, CHCl$_3$) δ 6.67 (d, 1H), 4.78-4.60 (m, 3H), 4.11 (s, 1H), 3.75 (s, 3H), , 2.55 (m, 2H), 2.24-2.00 (m, 5H), 1.56-1.40 (m, 15H).

(c) N-α-(tert-Butoxycarbonyl)-N-methoxy-N-methyl-L-isoleucinamide

A solution of N-α-(tert-butoxycarbonyl)-isoleucine (8.00 g, 33.3 mmol), O-benzotriazole-N,N,N',N'-tetramethyluronium-hexafluorophosphate (HBTU; 12.63 g; 33.3 mmol), DIEA (17.21 g, 133.2 mmol) in dimethylformamide (DMF, 35 mL) was stirred at room temperature for 2 minutes. To this solution was added N,O-dimethylhydroxylamine hydrochloride (3.25 g, 33.3 mmol), and the mixture was stirred at room temperature overnight. The solvent was removed in vacuo, and the residue was dissolved in EtOAc and washed with 5% citric acid (2 times), 5% Na$_2$CO$_3$ (2 times) and brine (2 times), dried over anhydrous MgSO$_4$, and filtered. The residue obtained after concentration was further purified by column chromatography on silica, eluting with EtOAc/hexanes (1:1). 8.5 g (Yield: 90%) of the title compound was obtained. $^1$H NMR (300 MHz, CDCl$_3$) δ 5.12 (d, 1H), 4.62 (m, 1H), 3.79 (s, 3H), 3.23 (s, 3H), 1.72 (m, 1H), 1.58 (m, 1H), 1.45 (s, 9H), 1.30-1.05 (m, 1H), 1.00-0.85 (m, 6H).

(d) N-α-(tert-Butoxycarbonyl)-L-isoleucinal

LiAlH$_4$ (0.20 g, 5.25 mmol) in 20 mL of anhydrous ether was stirred at room temperature for 30 minutes. The suspension was cooled to −45° C., and a solution of N-α-(tert-butoxycarbonyl)-N-methoxy-N-methyl-L-isoleucinamide (1.10 g, 3.89 mmol) in 6 mL of tetrahydrofuran (THF) was added dropwise to the suspension. The mixture was warmed to 0° C. and stirred for 2 hours. The mixture was then cooled to −45° C. To this solution was slowly added a solution of KHSO$_4$ (1.17 g) in H$_2$O (10 mL). The resulting mixture was filtered through Celite. The filtrate was washed with 5% citric acid (2 times) and brine (2 times), dried over anhydrous MgSO$_4$, filtered, and concentrated to dryness. 0.70 g of the title compound, as a colorless oil, was obtained and was immediately used in the next step without further purification.

(e) N-[N'-[2(S)-(tert-Butoxycarbonylamino)-3(S)-methylpentyl]-L-5,5-dimethylthiazolidine-4-carboxyl]-methionine methyl ester N-[(tert-Butoxycarbonyl)-L-5,5-dimethylthiazolidine-4-carboxyl]-L-methionine methyl ester (1.09 g, 2.68 mmol) was dissolved in a mixture of TFA (15 mL) and DCM (15 mL) and stirred at room temperature for 30 minutes. The solution was concentrated in vacuo. The resulting residue and N-α-(tert-butoxycarbonyl)-L-isoleucinal (0.70 g, 3.25 mmol) were dissolved in a mixture of methanol (MeOH; 30 mL) and acetic acid (0.6 mL). To this solution was added in portions sodium cyanoborohydride (0.204 g, 3.25 mmol) over a period of 30 minutes. MeOH was removed in vacuo. To the rest of the solution was added EtOAc and saturated NaHCO$_3$. The organic layer was separated and washed with saturated NaHCO$_3$ (1 time), water (1 time) and brine (1 time), dried over anhydrous MgSO$_4$, filtered, and concentrated. The residue obtained was further purified by column chromatography on silica, eluting with EtOAc/hexanes (1:2). 1.06 g (Yield: 78%) of the title compound was obtained. $^1$H NMR (300 MHz, CDCl$_3$) δ 8.70 (d, 1H), 4.68 (m, 1H), 4.53 (s, 2H), 3.90 (m, 1H), 3.79 (s, 1H), 3.75 (s, 3H), 3.42 (s, 1H), 2.95 (dd, 1H), 2.78 (dd, 1H), 2.50-2.70 (m, 2H), 2.22 (m, 2H), 2.13 (s, 3H), 1.60-1.40 (m, 12H), 1.36 (m, 2H), 1.38 (m, 2H), 0.92 (m, 9H); mass spectroscopy (electron spray) ((MS(ES)): 505.4, Calculated molecular weight (Calc. MW)=505.7.

(f) N-α-(tert -Butoxycarbonyl)-S-(triphenylmethyl)-L-cysteinal

The title compound was synthesized starting with N-α-(tert-butoxycarbonyl)-S-(triphenylmethyl)-L-cysteine by using the same procedure described in the synthesis of N-α-(tert-butoxycarbonyl)-L-isoleucinal.

(g) N-[N'-[2(S)-(2(R)-(tert-Butoxycarbonylamino)-3-triphenylmethyl-mercaptopropylamine)-3(S)-methylpentyl]-L-5,5-dimethylthiazolidine-4-carboxyl]-methionine methyl ester N-[N'-[2(S)-(tert-Butoxycarbonylamino)-3(S)-methylpentyl]-L-5,5-dimethylthiazolidine-4-carboxyl]-methionine methyl ester (1.06 g, 2.10 mmol) was dissolved in a mixture of trifluoroacetic acid (TFA; 15 mL) and DCM (15 mL) and stirred for 30 minutes at room temperature. The solution was concentrated in vacuo. The residue obtained and N-α-(tert -butoxycarbonyl)-S-(triphenylmethyl)-L-cysteinal (1.10 g, 2.46 mmol) were dissolved in a mixture of MeOH (15 mL) and HOAc (0.3 mL). To this was added in portions sodium cyanoborohydride (0.158 g, 2.52 mmol) over a period of 30 minutes. The mixture was stirred at room temperature overnight. 5 mL of saturated NaHCO$_3$ was added, and MeOH was removed in vacuo. To the rest of the solution was added EtOAc and saturated NaHCO$_3$. The organic layer was separated and washed with saturated NaHCO$_3$ (1 time) and brine (2 times), dried over anhydrous MgSO$_4$, and filtered. Concentration in vacuo gave the title compound, which was used directly in the next step without further purification. MS(ES): 836.5, Calc. MW=836.8.

(h) N-[N'-[2(S)-(2(R)-Amino-3-mercaptopropylamine)-3(S)-methylpentyl]-L-5,5-dimethylthiazolidine-4-carboxyl]-methionine N-[N'-[2(S)-(2(R)-(tert-Butoxycarbonylamino)-3-triphenylmethylmercaptopropylamine)-3(S)-methylpentyl]-L-5,5-dimethylthiazolidine-4-carboxyl]-methionine methyl ester (0.50 g, 0.42 mmol) was dissolved in a mixture of MeOH (16 mL) and 5N NaOH (4 mL) at 0° C. and stirred for 3 hours. The solution was neutralized to pH 7 by addition of 2N HCL. MeOH was removed in vacuo and EtOAc was added. The mixture was cooled to 0° C., and the aqueous layer was acidified to pH 2 by adding 2N HCl. The organic layer was separated, and the aqueous layer was extracted with EtOAc. The organic layers were pooled, washed with brine (1 time), dried over anhydrous MgSO$_4$, and filtered. The residue obtained after concentration in vacuo was dissolved in a mixture of trifluoroacetic acid (TFA; 6 mL), DCM (6 mL), and triethylsilane (0.6 mL). The solution was stirred at room temperature for 40 minutes. The residue after concentration in vacuo was partitioned between ether and 0.1% TFA aqueous solution. The aqueous layer was separated, purified on a preparative high performance liquid chromatography (HPLC) eluting with 0.1% TFA in H$_2$O/CH$_3$CN buffer, and lyophilized to give the title compound. MS(ES): 480.3, Calc. MW=480.8

EXAMPLE 2

N-[N'-[2(S)-(2(R)-Amino-3-mercaptopropylamine)-3(S)-methylpentyl]-L-5,5-dimethylthiazolidine-4-carboxyl]-methionine methyl ester (Compound 2)

N-[N'-[2(S)-(2(R)-(tert-Butoxycarbonylamino)-3-triphenylmethylmercaptopropylamine)-3(S)-methylpentyl]-L-5,5-dimethylthiazolidine-4-carboxyl]-methionine methyl ester (0.60 g, 0.718 mmol; Example 1(g)) was dissolved in a mixture of TFA (10 mL), DCM (10 mL), and triethylsilane (1 mL). The reaction mixture was stirred at room temperature for 30 minutes. The solution was concentrated in vacuo. The residue was partitioned between 1% TFA aqueous solution and ether. The aqueous layer was separated, purified by HPLC, and lyophilized to give the title compound. MS(ES): 494.3, Calc. MW=494.8.

EXAMPLE 3

N-[N'-[N"-(2(R)-Amino-3-mercaptopropyl)-tert-leucine]-L-5,5-dimethylthiazolidine-4-carboxyl]-methionine (Compound 3)

(a) N-[N'[(tert-Butoxycarbonyl)-tert-leucine]-L-5,5-dimethylthiazolidine-4-carboxyl]methionine methyl ester N-[(tert-Butoxycarbonyl)-L-5,5-dimethylthiazolidine-4-carboxyl]-methionine methyl ester (1.63 g; 4.01 mmol; Example 1(b)) was dissolved in a mixture of TFA (5 mL) and DCM (5 mL) and stirred at room temperature for 30 minutes. The solution was concentrated in vacuo. The residue was dissolved in toluene, and the solution was condensed in vacuo. This procedure was repeated three times and a white foam was obtained.

A solution of N-α-(tert-butoxycarbonyl)-tert-leucine (1.0 g, 4.01 mmol), EDC (0.769 g, 4.01 mmol), HOBt (0.650 g, 4.81 mmol), and DIEA (0.570 g, 4.41 mmol) in DCM (15 mL) was stirred at room temperature for 10 minutes. To it was added the above white foam. The mixture was stirred overnight. The solution was diluted with DCM (15 mL) and washed with 5% NaHCO$_3$ (2 times), 5% citric acid (2 times), and brine (2 times), dried over anhydrous MgSO$_4$, filtered, and concentrated in vacuo. The residue was purified by column chromatography, eluting with hexanes:EtOAc (2:1) and hexanes:EtOAc (1:1). 0.63 g of the title compound was obtained (Yield: 30%). 1H NMR (300 MHz, CDCl$_3$) δ 6.48 (d, 1H), 5.25 (d, 1H), 5.12 (d, 1H), 4.95-4.62 (m, 2H), 4.43-4.30 (m, 2H), 3.77 (s, 3H), 2.58 (m, 2H), 2.21, (m, 1H), 2.11 (s, 3H), 2.04 (m, 1H), 1.55-1.33 (m,12H), 1.12-0.94 (m, 12H).

(b) N-[N'-[N"-(2(R)-(tert-Butoxycarbonylamino)-3-triphenylmethyl-mercaptopropyl)-tert-leucine]-L-5,5-dimethylthiazolidine-4-carboxyl]-methionine methyl ester 0.6 g (1.15 mmol) of N-[N'-[tert-butoxycarbonyl)-tert-leucine]-L-5,5-dimethylthiazolidine-4-carboxyl]-methionine methyl ester was dissolved in a mixture of TFA (5 mL), DCM (5 mL) and triethylsilane (Et$_3$SiH) (1 mL) and stirred at room temperature for 30 minutes. The solution was concentrated in vacuo. The residue was dissolved in toluene, and the solution was condensed to dryness. This procedure was repeated until a white foam was obtained (4 times). This foam and 0.5 g (1.12 mmol) of N-α-(tert-butoxycarbonyl)-S-(triphenylmethyl)-L-cysteinal (Example 1(f)) were dissolved in 4 mL of methanol and 0.2 mL of acetic acid. To this mixture was added NaBH$_3$CN (72 mg, 1.15 mmol), and it was stirred for 30 minutes. 0.5 g (1.12 mmol) of N-α-(tert-butoxycarbonyl)-S-(triphenylmethyl)-L-cysteinal and 72 mg (1.15 mmol) of NaBH$_3$CN were added. The reaction mixture was stirred for 30 minutes. 0.5 g (1.12 mmol) of N-α-(tert-butoxycarbonyl)-S-(triphenylmethyl)-L-cysteinal and 72 mg (1.15 mL) of NaBH$_3$CN were then added followed by addition of 0.1 mL of acetic acid. The solution was stirred overnight and concentrated in vacuo. The residue was dissolved in EtOAc and washed with saturated NaHCO$_3$ (2 times) and brine (2 times), dried over anhydrous MgSO$_4$, filtered, and condensed in vacuo. The residue was purified by using column chromatography (silica), eluting with EtOAc:hexanes (1:2) and EtOAc:hexanes (1:1). 930 mg (Yield: 95%) of the title compound, as a white solid, was obtained. MS(ES): 850.5 Calc. MW=850.8

(c) N-[N'-[N"(2(R)-Amino-3-mercaptopropyl)-tert-leucine]-L-5,5-dimethylthiazolidine-4-carboxyl]-methionine 230 mg (0.27 mmol) of N-[N'-[N"-(2(R)-(tert-butoxycarbonylamino)-3-triphenylmethyl-mercaptopropyl)-tert-leucine]-L-5,5-dimethylthiazolidine-4-carboxyl]-methionine methyl ester was dissolved in 2 mL of methanol at 0° C. To it was added 0.4 mL of 1N KOH solution. The white precipitate was dissolved by addition of 0.8 mL of THF. The mixture was warmed to room temperature and stirred for 1.5 hours. To the solution was added 2N HCl at 0° C. until the pH was about 2. The solution was diluted to 25 mL by addition of EtOAc and then 10 mL of brine was added. The organic layer was separated, dried over anhydrous MgSO$_4$, filtered, and concentrated in vacuo to give a white solid (220 mg). The white solid was dissolved in a mixture of 5 mL of DCM and 1 mL of triethylsaline (Et$_3$SiH). To it was added 5 mL of TFA, and the solution was stirred for 40 minutes. The solution was concentrated in vacuo. The white solid was triturated with hexanes and then dissolved in 0.1% TFA aqueous solution. It was purified on a preparative HPLC and lyophilization gave the title compound (47 mg; Yield: 36%). $^1$H NMR (300 MHz, CDCl$_3$) δ 6 8.28 (d, 1H), 5.02 (d, 1H), 4.74 (d, 1H), 4.66 (m, 1H), 4.53 (s, 1H), 4.47 (m, 1H), 3.30 (m, 2H), 2.77 (m, 2H), 2.58 (m, 1H), 2.51 (m, 4H), 2.03 (m, 4H), 1.82 (m, 1H) 1.54 (s, 2H), 1.38 (s, 3H), 1.03-0.88 (m, 12H); MS (ES): 494.2, Calc. MW=494.7

EXAMPLE 4

N-[N'-[N"-(2(R)-Amino-3-mercaptopropyl)-tert-leucine]-L-5,5-dimethylthiazolidine-4-carboxyl]-methionine methyl ester (Compound 4)

660 mg (0.776 mmol) of N-[N'-[N"-(2(R)-(tert-butoxycarbonyl-amino)-3-triphenylmethyl-mercaptopropyl)-tert-leucine]-L-5,5-dimethylthiazplidine-4-carboxyl]-methionine methyl ester (Example 3(b)) was dissolved in a mixture of DCM (5 mL) and Et$_3$SiH (1 mL). To it was added 5 mL of TFA. The mixture was stirred at room temperature for 0.5 hours. The solution was concentrated in vacuo. The residue was triturated with hexanes and then dissolved in 0.1% TFA aqueous solution. It was purified by a preparative HPLC, eluting with a gradient (buffer A: 0.1% TFA in H$_2$O, buffer B: 0.1% TFA in CH$_3$CN). Lyophilization gave the title compound as a white solid (310 mg; Yield: 78%). MS (ES): 508.3, Calc. MW=508.8.

EXAMPLE 5

N-[N'-[N"-(2(R)-Amino-3-mercaptopropyl)-tert-leucine]-L-5,5-dimethylthiazolidine-4-carboxyl]-leucine (Compound 5)

The title compound was synthesized by using an analogus procedure described in the synthesis of Example 3. MS(ES): 476.2, Calc. MW=476.3.

EXAMPLE 6

N-[N'-[N"-(2(R)-Amino-3-mercaptopropyl)-tert-leucine]-L-5,5-dimethylthiazolidine-4-carboxyl]-leucine-methyl ester The title compound was synthesized by using an analogous procedure described in the synthesis of Example 4. MS(ES):490.3, Calc. MW=490.7.

EXAMPLE 7

N-[N'-[N"-(2(R)-Amino-3-mercaptopropyl)-valine]-L-5,5-dimethylthiazolidine-4-carboxyl]-leucine (Compound 7)

The title compound was synthesized by using an analogous procedure described in the synthesis of Example 3. MS(ES): 462.4, Calc. MW=462.7.

EXAMPLE 8

N-[N'-[N"-(2(R)-Amino-3-mercaptopropyl)-valine]-L-5,5-dimethylthiazolidine-4-carboxyl]-leucine-methyl ester (Compound 8)

The title compound was synthesized by using an analogous procedure described in the synthesis of Example 4. MS(ES): 476.3, Calc. MW=476.7.

EXAMPLE 9

N-[N'-[N"-(2(R)-Amino-3-mercaptopropyl)-valine]-L-5,5-dimethylthiazolidine-4-carboxyl]-methionine (Compound 9)

The title compound was synthesized by using an analogous procedure described in the synthesis of Example 3. MS(ES): 480.3, Calc. MW=480.7.

EXAMPLE 10

N-[N'-[N"-(2(R)-Amino-3-mercaptopropyl)-valine]-L-5,5-dimethylthiazolidine-4-carboxyl]-methionine-methyl ester (Compound 10)

The title compound was synthesized by using an analogous procedure described in the synthesis of Example 4. MS(ES): 494.3, Calc. MW=494.8.

EXAMPLE 11

[N-(2(R)-Amino-3-mercaptopropyl)-L-5,5-dimethylthiazolidine-4-carboxyl]-2,3-dichlorobenzamide (Compound 11)

(a) [(tert-Butoxycarbonyl)-L-5,5-dimethylthiazolidine-4-carboxyl]-2,3-dichlorobenzamide A solution of N-α-(tert-butoxycarbonyl)-L-5,5-dimethylthiazolidine-4-carboxylic acid (0.65 g, 2.50 mmol; Example 1(a)), HBTU (0.948 g, 2.50 mmol), and DIEA (1.3 g, 10 mmol) in DMF (25 mL) was stirred at room temperature for 3 minutes. To it was added 2,3-dichlorobenzylamine (0.44 g, 2.50 mmol). The mixture was stirred overnight. The solvent was removed in vacuo, and the residue was dissolved in EtOAc, washed with 5% NaHCO₃ (2 times), 5% citric acid (2 times), and brine (2 times), dried over anhydrous MgSO₄, filtered, and concentrated in vacuo. The title compound (0.83 g; Yield: 79%) was obtained after chromatography (silica) with EtOAc:hexanes (1:2). $^1$H NMR (300 MHz, CDCl₃) δ 7.40 (m, 2H), 7.18 (m, 1H), 6.55 (bs, 1H), 4.65 (m, 3H), 4.52 (m, 1H), 4.07 (s, 1H), 1.58 (s, 3H), 1.20, (m, 12H).

(b) [N-(2(R)-Amino-3-mercaptopropyl)-L-5,5-dimethylthiazolidine-4-carboxyl]-2,3-dichlorobenzamide

[(tert-Butoxycarbonyl)-L-5,5-dimethylthiazolidine-4-carboxyl]-2,3-dischlorobenzamide (0.419 g, 1 mmol) was dissolved in 10 mL of 50% TFA in DCM. The mixture was stirred at room temperature for 0.5 hours. TFA and the solvent were removed in vacuo. The residue and N-α-(tert-butoxycarbonyl)-S-(triphenylmethyl)-L-cysteinal (2 mmol; Example 1(f)) were dissolved in MeOH (10 mL) and HOAc (0.2 mL). To it was added in portions sodium cyanoborohydride (94 mg, 1.5 mmol). The mixture was stirred at room temperature overnight. The solvents were removed in vacuo, and the residue was dissolved in EtOAc. The solution was washed with 5% NaHCO₃ (2 times), 5% citric acid (2 times) and brine (2 times), dried over anhydrous MgSO₄, filtered, and concentrated in vacuo. The residue was dissolved in 15 mL of DCM and 2 mL of triisopropylsilane. To the solution was added 10 mL of TFA. The reaction mixture was stirred at room temperature for 0.5 hours. The solution was condensed in vacuo, and the resulting residue was partitioned between 0.1% TFA aqueous solution and EtOAc. The organic layer was concentrated in vacuo. The residue was triturated with hexanes and then purified by HPLC. Lyophilization gave the title compound (339 mg; Yield: 83%). MS (ES): 407.0, Calc. MW=407.4. $^1$H NMR (300 MHz, CDCl₃) δ 8.21 (bs, 2H), 7.61 (t, 1H), 7.41 (dd, 1H), 7.27 (dd, 1H), 7.19 (dd, 1H), 4.55 (d, 2H), 4.43 (d, 1H), 3.88, (d, 1H), 3.28 (s, 1H), 3.22 (m, 1H), 3.10 (m, 2H), 2.79 (m, 2H), 1.73 (bs, 1H), 1.57 (s, 3H), 1.38 (s, 3H).

EXAMPLE 12

[N-(2(R)-Amino-3-mercaptopropyl)-L-5,5-dimethylthiazolidine-4-carboxyl]-naphthylmethyl amide (Compound 12)

The title compound was synthesized by using an analogous procedure to Example 11. MS(ES): 389.1, Calc. NW=389.6 $^1$H NMR (300 MHz, CDCl₃) δ 8.15 (d, 1H), 7.90 (m, 1H), 7.82 (d, 1H), 7.61-7.41 (m, 5H), 5.22 (dd, 1H), 4.63 (dd, 1H), 4.39 (d, 1H), 3.78 (d, 1H), 3.24 (s, 1H), 2.97 (m, 2H), 2.76 (m, 1H), 2.48 (m, 2H), 1.57 (s, 3H), 1.40 (s, 3H), 1.28 (m, 1H).

OTHER EMBODIMENTS

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:
1. A compound of formula I or formula II

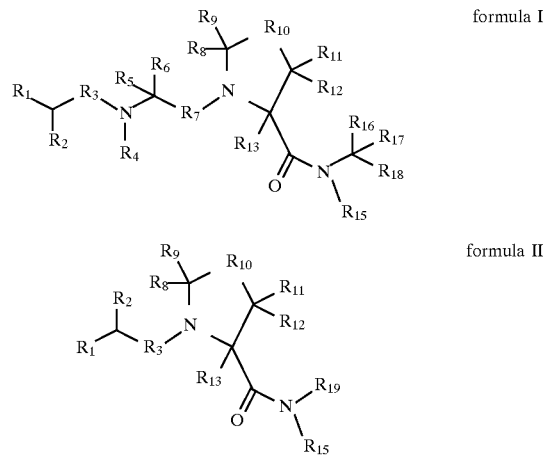

wherein
$R_1$ is H or $NR_{20}R_{21}$;
$R_2$ is $(CH_2)_mSR_{22}$, $(CH_2)_mSSR_{22}$, substituted or unsubstituted heterocycle, or substituted or unsubstituted heterocycle lower alkyl, where m is 1–6 and said substituent is lower alkyl, lower alkenyl, aryl, or aryl lower alkyl;
each of $R_3$ and $R_7$, independently, is $CH_2$ or $C(O)$;
each of $R_4$ and $R_{15}$, independently, is H or lower alkyl;
each of $R_5$ and $R_{16}$, independently, is H or a substituted or unsubstituted moiety selected from lower alkyl, thio lower alkyl, lower alkenyl, thio lower alkenyl, cycloalkyl, cycloalkyl lower alkyl, aryl, and aryl lower alkyl, where said substituent is lower alkyl, hydroxy, halo, $C(O)NR_{23}R_{24}$, or COOH;
each of $R_6$, $R_8$, $R_9$, $R_{11}$, $R_{12}$, $R_{13}$, and $R_{17}$, independently, is H or a substituted or unsubstituted moiety selected from lower alkyl, lower alkenyl, thio lower alkyl, cycloalkyl, aryl, and aryl lower alkyl, where said substituent is lower alkyl, halo, hydroxy, $C(O)NR_{25}R_{26}$, or COOH;
$R_{10}$ is S, SO, or $SO_2$;
$R_{18}$ is $COOR_{27}$ or $C(O)NR_{28}R_{29}$, or, together with $R_{16}$, forms —COOCH₂CH₂—.
$R_{19}$ is a substituted or unsubstituted moiety selected from lower alkyl, lower alkenyl, aryl, and aryl lower alkyl, where said substituent is lower alkyl, halo, or alkoxy; and
each of $R_{20}$, $R_{21}$, $R_{22}$, $R_{23}$, $R_{24}$, $R_{25}$, $R_{26}$, $R_{27}$, $R_{28}$, and $R_{29}$, independently, is H or lower alkyl;
provided that if $R_2$ is $(CH_2)_mSH$ and $R_5$ is thio lower alkyl, the free thio groups of $R_2$ and $R_5$ can form a disulfide bond; or a pharmaceutically acceptable salt thereof.

2. A compound of claim 1, wherein said compound has formula I; or a pharmaceutically acceptable salt thereof.

3. A compound of claim 1, wherein said compound has formula II; or a pharmaceutically acceptable salt thereof.

4. A compound of claim 2, wherein $R_2$ is $(CH_2)_mSR_{22}$, heterocycle, or heterocycle lower alkyl; each of $R_4$ and $R_{15}$, independently, is H; $R_5$ is lower alkyl; $R_6$ is H; each of $R_8$, $R_9$, $R_{11}$, and $R_{12}$, independently, is H or lower alkyl; $R_{10}$ is S; $R_{13}$ is H; $R_{16}$ is lower alkyl or substituted thio lower alkyl wherein said substituent is lower alkyl; and $R_{17}$ is H; or a pharmaceutically acceptable salt thereof.

5. A compound of claim 4, wherein $R_1$ is $NR_{20}R_{21}$ and $R_2$ is $(CH_2)_mSR_{22}$; or a pharmaceutically acceptable salt thereof.

6. A compound of claim 5, wherein $R_3$ is $CH_2$; each of $R_8$ and $R_9$, independently, is H; and $R_{18}$ is $COOR_{27}$; or a pharmaceutically acceptable salt thereof.

7. A compound of claim 6, wherein $R_1$ is $NH_2$; $R_2$ is $CH_2SH$; $R_5$ is $CH(CH_3)(CH_2CH_3)$, $CH(CH_3)_2$, or $C(CH_3)_3$; each of $R_{11}$ and $R_{12}$, independently, is $CH_3$; $R_{16}$ is $(CH_2)_2SCH_3$, $(CH_2)_3CH_3$, or $CH_2CH(CH_3)_2$; and $R_{18}$ is COOH or $COOCH_3$; or a pharmaceutically acceptable salt thereof.

8. A compound of claim 4, wherein $R_1$ is H; and $R_2$ is heterocycle or heterocycle lower alkyl; or a pharmaceutically acceptable salt thereof.

9. A compound of claim 8, wherein $R_3$ is $CH_2$; each of $R_8$ and $R_9$, independently, is H; and $R_{18}$ is $COOR_{27}$; or a pharmaceutically acceptable salt thereof.

10. A compound of claim 9, wherein $R_2$ is imidazolyl or imidazolyl lower alkyl; $R_5$ is $CH(CH_3)(CH_2CH_3)$, $CH(CH_3)_2$, or $C(CH_3)_3$; each of $R_{11}$ and $R_{12}$, independently, is $CH_3$; $R_{16}$ is $(CH_2)_2SCH_3$, $(CH_2)_3CH_3$, or $CH_2CH(CH_3)_2$; and $R_{18}$ is COOH or $COOCH_3$; or a pharmaceutically acceptable salt thereof.

11. A compound of claim 3, wherein $R_2$ is $(CH_2)_mSR_{20}$, heterocycle, or heterocycle lower alkyl; each of $R_8$, $R_9$, $R_{11}$, and $R_{12}$, independently, is H or lower alkyl; $R_{10}$ is S; $R_{13}$ is H; and $R_{15}$ is H; or a pharmaceutically acceptable salt thereof.

12. A compound of claim 11, wherein $R_1$ is $NR_{20}R_{21}$; and $R_2$ is $(CH_2)_mSR_{22}$; or a pharmaceutically acceptable salt thereof.

13. A compound of claim 12, wherein $R_3$ is $CH_2$; $R_8$ and $R_9$ are H; and $R_{19}$ is substituted or unsubstituted aryl lower alkyl where said substituent is halo or lower alkyl; or a pharmaceutically acceptable salt thereof.

14. A compound of claim 13, wherein $R_1$ is $NH_2$; $R_2$ is $CH_2SH$; each of $R_{11}$ and $R_{12}$, independently, is $CH_3$; and $R_{19}$ is 2,3-dichlorobenzyl or 1-naphthylmethyl; or a pharmaceutically acceptable salt thereof.

15. A compound of claim 11, wherein $R_1$ is H and $R_2$ is heterocycle or heterocycle lower alkyl; or a pharmaceutically acceptable salt thereof.

16. A compound of claim 15, wherein $R_3$ is $CH_2$; each of $R_8$ and $R_9$, independently, is H; and $R_{19}$ is substituted or unsubstituted aryl lower alkyl where said substituent is halo or lower alkyl; or a pharmaceutically acceptable salt thereof.

17. A compound of claim 16, wherein $R_2$ is imidazolyl or imidazolyl lower alkyl; each of $R_{11}$ and $R_{12}$, independently, is $CH_3$; and $R_{19}$ is 2,3-dichlorobenzyl or 1-napthylmethyl; or a pharmaceutically acceptable salt thereof.

18. A compound of claim 1, said compound being of the formula:

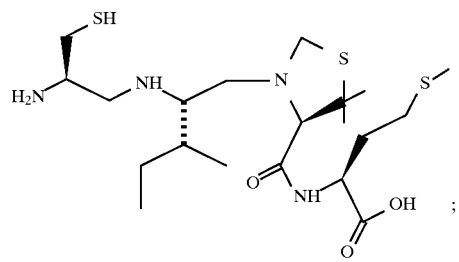

-continued

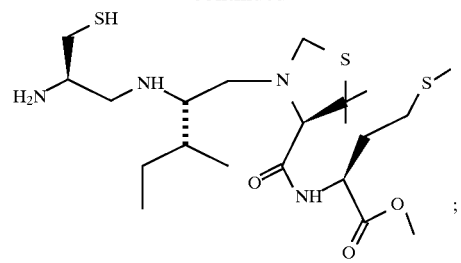

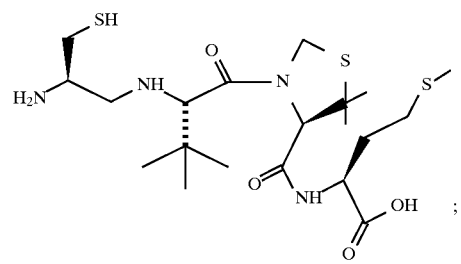

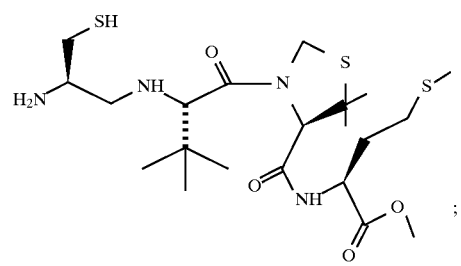

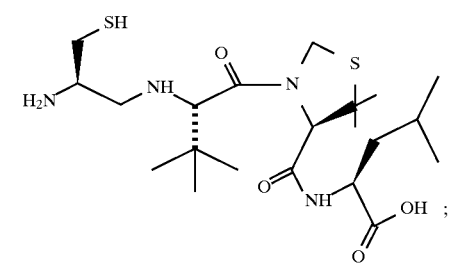

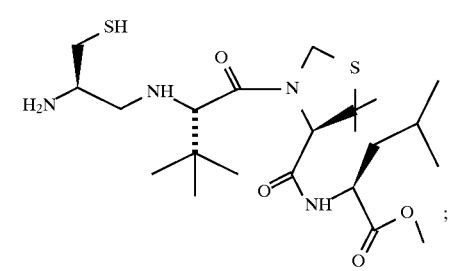

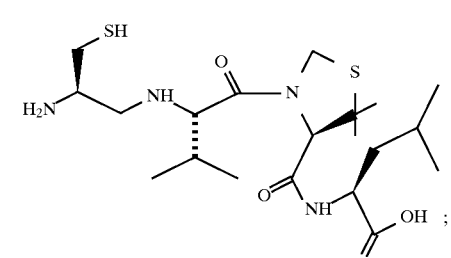

-continued

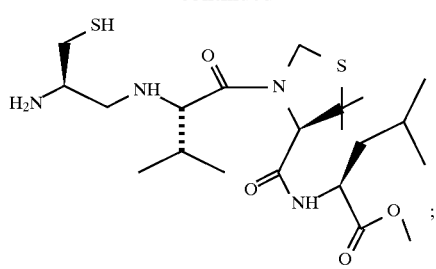

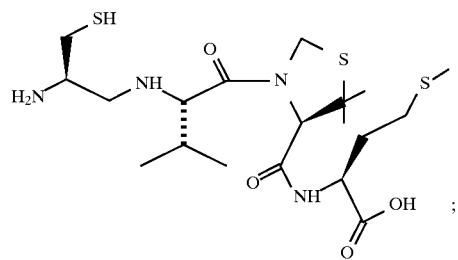

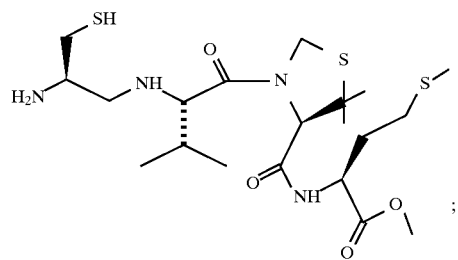

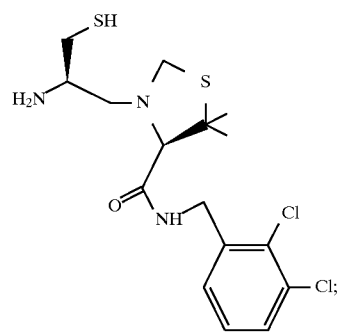

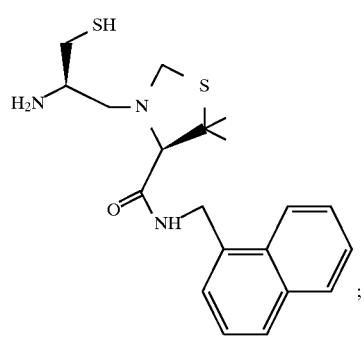

-continued

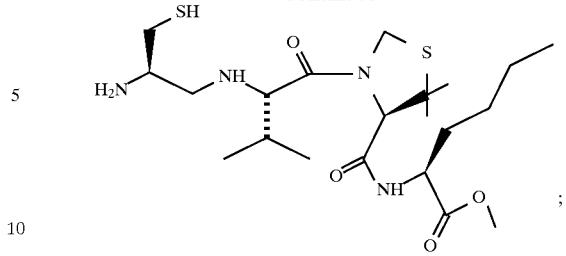

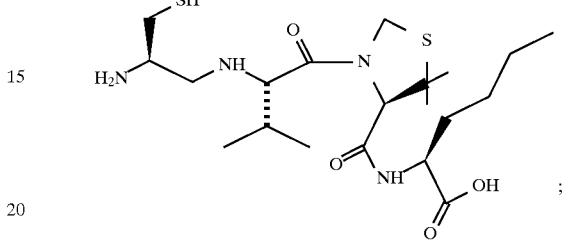

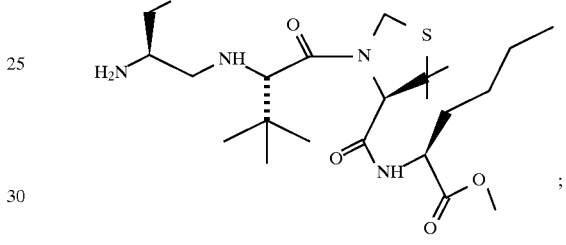

and

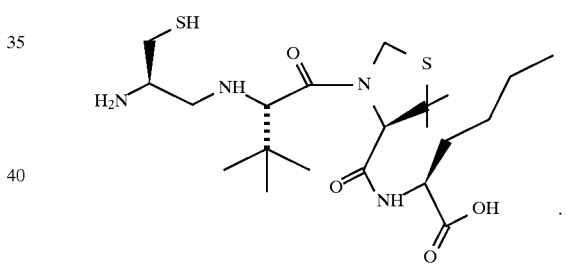

19. A compound consisting of a first moiety and a second moiety, wherein each of said first and second moieties, independently, is of formula I or formula II of claim 1 except that each $R_2$ of said first moiety and $R_2$ of said second moiety, independently, are —$(CH_2)_m S$— and form a disulfide bond; or a pharmaceutically acceptable salt thereof.

20. A compound of claim 19 wherein said first and second moieties are identical; or a pharmaceutically acceptable salt thereof.

21. A method of treating tumors or restenosis in a subject in need of said treatment, which comprises administering to said subject a therapeutically effective amount of the compound or salt of claim 1.

22. A method of treating tumors or restenosis in a subject in need of such treatment, which comprises administering to said subject a therapeutically effective amount of a compound or salt according to claim 18.

23. A method of treating tumors or restenosis in a subject in need of such treatment, which comprises administering to said subject a therapeutically effective amount of a compound or salt according to claim 19.

* * * * *